United States Patent
De Kock et al.

(10) Patent No.: US 9,572,975 B2
(45) Date of Patent: Feb. 21, 2017

(54) PADDLE LEADS CONFIGURED FOR SUTURE FIXATION

(71) Applicant: Cardiac Pacemakers, Inc., St. Paul, MN (US)

(72) Inventors: Andrew L. De Kock, Andover, MN (US); Brian Soltis, St. Paul, MN (US); Eric A. Mokelke, Flagstaff, AZ (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/843,836

(22) Filed: Sep. 2, 2015

(65) Prior Publication Data

US 2016/0059005 A1 Mar. 3, 2016

Related U.S. Application Data

(60) Provisional application No. 62/044,459, filed on Sep. 2, 2014.

(51) Int. Cl.
*A61N 1/00* (2006.01)
*A61N 1/05* (2006.01)
*A61N 1/36* (2006.01)

(52) U.S. Cl.
CPC .......... *A61N 1/0553* (2013.01); *A61N 1/0558* (2013.01); *A61N 1/36117* (2013.01)

(58) Field of Classification Search
CPC . A61N 1/0553; A61N 1/0558; A61N 1/36117
See application file for complete search history.

(56) References Cited

U.S. PATENT DOCUMENTS

| | | | |
|---|---|---|---|
| 5,476,493 A | 12/1995 | Muff | |
| 6,564,079 B1 | 5/2003 | Cory et al. | |
| 6,985,774 B2 | 1/2006 | Kieval et al. | |
| 7,015,061 B2 | 3/2006 | Lu et al. | |
| 7,337,005 B2* | 2/2008 | Kim | A61N 1/0558 607/117 |
| 7,445,953 B2 | 11/2008 | Lu et al. | |

(Continued)

FOREIGN PATENT DOCUMENTS

| | | |
|---|---|---|
| CN | 101244315 A | 8/2008 |
| EP | 2108398 B1 | 10/2009 |

(Continued)

OTHER PUBLICATIONS

International Preliminary Report on Patentability issued in PCT/US2014/046008, mailed Jan. 28, 2016, 8 pages.

(Continued)

*Primary Examiner* — George Manuel
(74) *Attorney, Agent, or Firm* — Faegre Baker Daniels LLP

(57) ABSTRACT

Various embodiments concern an implantable paddle lead. The paddle can be attached to a distal portion of an elongate lead body. The paddle can comprise a main panel and a ridge that peripherally surrounds the main panel. The main panel can comprise a first face and a second face opposite the first face. One or more electrodes can be exposed on the first face but not exposed on the second face. The paddles can be sutured to anatomical structures. The sutures can be threaded through the main panel but not through the ridge. The paddle can be thicker along the ridge than along the main panel.

35 Claims, 17 Drawing Sheets

(56) References Cited

U.S. PATENT DOCUMENTS

| | | |
|---|---|---|
| 7,502,650 B2 | 3/2009 | Kieval |
| 7,616,997 B2 | 11/2009 | Kieval et al. |
| 7,813,812 B2 | 10/2010 | Kieval et al. |
| 8,126,560 B2 | 2/2012 | Scheiner et al. |
| 8,175,705 B2 | 5/2012 | Libbus |
| 8,571,664 B2 | 10/2013 | Anderson et al. |
| 8,901,268 B2 | 12/2014 | Krishnamoorthy et al. |
| 8,948,872 B2 | 2/2015 | Shuros et al. |
| 9,345,877 B2 | 5/2016 | Pignato et al. |
| 2002/0095080 A1 | 7/2002 | Cory et al. |
| 2003/0187490 A1 | 10/2003 | Gliner |
| 2004/0176759 A1 | 9/2004 | Krishnamurthy et al. |
| 2005/0085884 A1 | 4/2005 | O'Brien et al. |
| 2005/0096710 A1 | 5/2005 | Kieval |
| 2005/0182456 A1 | 8/2005 | Ziobro et al. |
| 2006/0085049 A1 | 4/2006 | Cory et al. |
| 2006/0276704 A1 | 12/2006 | McGinnis et al. |
| 2007/0021792 A1 | 1/2007 | Kieval et al. |
| 2007/0027512 A1 | 2/2007 | Chan et al. |
| 2007/0208391 A1 | 9/2007 | Wahlstrand et al. |
| 2008/0004673 A1 | 1/2008 | Rossing et al. |
| 2008/0046051 A1 | 2/2008 | Skubitz et al. |
| 2008/0147146 A1 | 6/2008 | Wahlgren et al. |
| 2009/0132002 A1 | 5/2009 | Kieval |
| 2009/0143837 A1 | 6/2009 | Rossing et al. |
| 2009/0234418 A1 | 9/2009 | Kieval et al. |
| 2010/0324641 A1 | 12/2010 | Skubitz et al. |
| 2011/0257716 A1 | 10/2011 | Tiedtke |
| 2013/0018247 A1 | 1/2013 | Glenn et al. |
| 2015/0018918 A1 | 1/2015 | Mokelke et al. |
| 2015/0165215 A1 | 6/2015 | Mokelke et al. |
| 2015/0231391 A1 | 8/2015 | Mokelke et al. |
| 2015/0366465 A1 | 12/2015 | De Kock et al. |
| 2015/0366467 A1 | 12/2015 | De Kock et al. |
| 2016/0074650 A1 | 3/2016 | De Kock et al. |

FOREIGN PATENT DOCUMENTS

| | | |
|---|---|---|
| EP | 1487535 B1 | 6/2012 |
| KR | 20120053090 A | 5/2012 |
| WO | 0226314 A1 | 4/2002 |
| WO | 2007118090 A2 | 10/2007 |
| WO | 2015195980 A1 | 12/2015 |
| WO | 2015195982 A2 | 12/2015 |

OTHER PUBLICATIONS

International Search Report and Written Opinion issued in PCT/US2015/036526, mailed Oct. 26, 2015, 12 pages.
International Search Report and Written Opinion Issued in PCT/US2015/036528, mailed Jan. 19, 2016, 15 pages.
International Search Report and Written Opinion issued in PCT/US2015/050303, mailed Jan. 14, 2016, 12 pages.
International Search Report and Written Opinion] issued in PCT/US2014/046008, mailed Oct. 1, 2014, 12 pages.
Invitation to Pay Additional Fees and, Where Applicable, Protest Fee issued in PCT/US2015/036528, mailed Oct. 28, 2015, 6 pages.

* cited by examiner

PADDLE LEADS CONFIGURED FOR SUTURE FIXATION

CROSS-REFERENCE TO RELATED APPLICATION

This application claims priority to Provisional Application No. 62/044,459, filed Sep. 2, 2014, which is herein incorporated by reference in its entirety.

TECHNICAL FIELD

The present disclosure is directed to systems for stimulating anatomical structures. More particularly, the present disclosure is directed to paddle leads that can be securely sutured to anatomical structures that are targeted for electrical stimulation.

BACKGROUND

Implantable pulse generators have been used to stimulate a variety of anatomical structures, such as the heart, the brain, the spinal cord, and nerves, among other targets. Electrical energy is typically conveyed from the implantable pulse generator to the targeted tissue via a lead. A variety of types of leads have been developed for these purposes. In order to maintain the ability to deliver reliable chronic therapy, the lead may need to be securable within the body, such as proximate the targeted tissue. A lack of reliable anchoring can lead to an inability to stimulate targeted tissue and/or unintended stimulation of non-targeted tissue.

SUMMARY

In example 1, an implantable lead comprising: an elongated lead body having a proximal portion and a distal portion; at least one conductor extending within the elongated lead body; at least one electrode electrically connected to the at least one conductor; and a paddle attached to the distal portion of the lead body, the paddle comprising a main panel and a ridge on a periphery of the main panel, the main panel comprising a first face and a second face opposite the first face, the at least one electrode exposed on the first face, wherein the paddle is thicker along the ridge than along the main panel.

In example 2, the lead of example 1, wherein the ridge is raised from the first face of the main panel.

In example 3, the lead of either of examples 1 or 2, wherein the paddle comprises a distal side, a first lateral side, and a second lateral side opposite the first lateral side, and wherein the ridge peripherally surrounds the main panel on the distal side, the first lateral side, and the second lateral side of the paddle.

In example 4, the lead of example 3, wherein the first and the second lateral sides are configured to wrap partially around an anatomical structure.

In example 5, the lead of example 4, wherein the anatomical structure is a blood vessel.

In example 6, the lead of any preceding example, wherein each of the at least one electrode is not exposed on the second face.

In example 7, the lead of any preceding example, wherein the ridge has greater tear resistance than the main panel.

In example 8, the lead of any preceding example, further comprising a raised pattern of traces formed on the second face.

In example 9, the lead of example 8, wherein the main panel, the ridge, and the raised pattern of traces form a unitary member that is molded from a first polymeric material.

In example 10, the lead of either of examples 8 or 9, wherein the ridge is raised higher above the second face than the raised pattern of traces.

In example 11, the lead of any of examples 8-10, wherein the raised pattern of traces comprises a plurality of concentric ovals.

In example 12, the lead of any of examples 8-10, wherein the raised pattern of traces comprises a grid pattern of a first set of parallel traces that intersect a second set of parallel traces.

In example 13, the lead of any of examples 8-12, wherein a plurality of grooves are formed through the raised pattern of traces, the plurality of grooves extending parallel with a longitudinal axis of the paddle.

In example 14, the lead of any preceding example, wherein: the paddle is configured to be secured to tissue by at least one suture that extends through the main panel from the first face to the second face, and the ridge is configured to block propagation of tears in the main panel due to the at least one suture from propagating through the ridge.

In example 15, the lead of any preceding example, further comprising a winged portion attached to the lead body, the winged portion located proximally of the paddle, the winged portion comprising a first wing and a second wing laterally opposite the first wing, wherein each of the first wing and the second wing comprise an inner portion and an outer portion that surrounds the inner portion, the inner portion thinner than the outer portion.

In example 16, an implantable lead comprising: an elongated lead body having a proximal portion and a distal portion; at least one conductor extending within the elongated lead body; at least one electrode electrically connected to the at least one conductor; and a paddle attached to the distal portion of the lead body, the paddle comprising a main panel and a ridge on a periphery of the main panel, the main panel comprising a first face and a second face opposite the first face, each of the at least one electrode exposed on the first face but not exposed on the second face, wherein the paddle is thicker along the ridge than along the main panel.

In example 17, the lead of example 16, wherein the ridge is raised from the first face of the main panel.

In example 18, the lead of either of examples 16 or 17, wherein the paddle comprises a distal side, a first lateral side, and a second lateral side opposite the first lateral side, and wherein the ridge peripherally surrounds the main panel on the distal side, the first lateral side, and the second lateral side of the paddle.

In example 19, the lead of example 18, wherein the first and the second lateral sides are configured to wrap partially around an anatomical structure.

In example 20, the lead of example 19, wherein the anatomical structure is a blood vessel.

In example 21, the lead of any of examples 16-20, wherein the main panel and the ridge are formed by a unitary member that is molded from a first polymeric material.

In example 22, the lead of any of examples 16-21, wherein the ridge has greater tear resistance than the main panel.

In example 23, the lead of any of examples 16-22, further comprising a raised pattern of traces formed on the second face.

In example 24, the lead of example 23, wherein the main panel, the ridge, and the raised pattern of traces form a unitary member that is molded from a first polymeric material.

In example 25, the lead of either of examples 23 or 24, wherein the ridge is raised higher above the second face than the raised pattern of traces.

In example 26, the lead of any of examples 23-25, wherein the raised pattern of traces comprises a plurality of concentric ovals.

In example 27, the lead of any of examples 23-25, wherein the raised pattern of traces comprises a grid pattern of a first set of parallel traces that intersect a second set of parallel traces.

In example 28, the lead of any of examples 23-27, wherein a plurality of grooves are formed through the raised pattern of traces, the plurality of grooves extending parallel with a longitudinal axis of the paddle.

In example 29, the lead of any of examples 16-28, wherein: the paddle is configured to be secured to tissue by at least one suture that extends through the main panel from the first face to the second face, and the ridge is configured to block propagation of tears in the main panel due to the at least one suture from propagating through the ridge.

In example 30, the lead of any of examples 16-29, further comprising a winged portion attached to the lead body, the winded portion located proximally of the paddle, the winged portion comprising a first wing and a second wing laterally opposite the first wing, wherein each of the first wing and the second wing comprise an inner portion and an outer portion that surrounds the inner portion, the inner portion thinner than the outer portion.

In example 31, an implantable device comprising: at least one electrode; and a paddle including the at least one electrode and a planar member attached to the at least one electrode, the planar member comprising a main panel and a ridge on a periphery of the main panel, each of the at least one electrode exposed on a face of the main panel, the ridge thicker than the main panel.

In example 32, the lead of example 31, wherein the planar member comprises a step that transitions the relatively thinner main panel to the relatively thicker ridge.

In example 33, the lead of either of examples 31 or 32, wherein: the paddle is configured to be secured to tissue by at least one suture that extends through the main panel, and the ridge is configured to block propagation of tears in the main panel from propagating through the ridge.

In example 34, the lead of any of examples 31-33, wherein the planar member further comprises a raised pattern of traces formed on the main panel from a polymeric material.

In example 35, a method of implanting a lead comprising: introducing an elongated lead into a patient, the lead comprising a paddle that comprises a main panel and a ridge that peripherally surrounds the main panel, wherein the paddle is thicker along the ridge than along the main panel; wrapping opposing lateral sides of the paddle partially around an anatomical structure; and suturing the paddle to the anatomical structure with a plurality of sutures, each of the sutures threaded through the main panel but not through the ridge, wherein the ridge is configured to block propagation of tears in the main panel from propagating through the ridge.

While multiple embodiments are disclosed, still other embodiments within the scope of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The present disclosure concerns leads for stimulating anatomical structures. While the carotid sinus is used as an exemplar herein for demonstrating lead features, it will be understood that leads according to the present disclosure can be used in conjunction with other anatomical structures. Such structures can include, but are not limited to, nerves, the heart, the spinal cord, the brain, gastrointestinal structures, pelvic structures, and the diaphragm, among others. For example, a lead according to the present disclosure may be used to stimulate the vagus nerve. In another example, a lead according to the present disclosure may be used in an epicardial application. Other applications for the leads are also contemplated as being within the scope of this disclosure.

Figure 1:
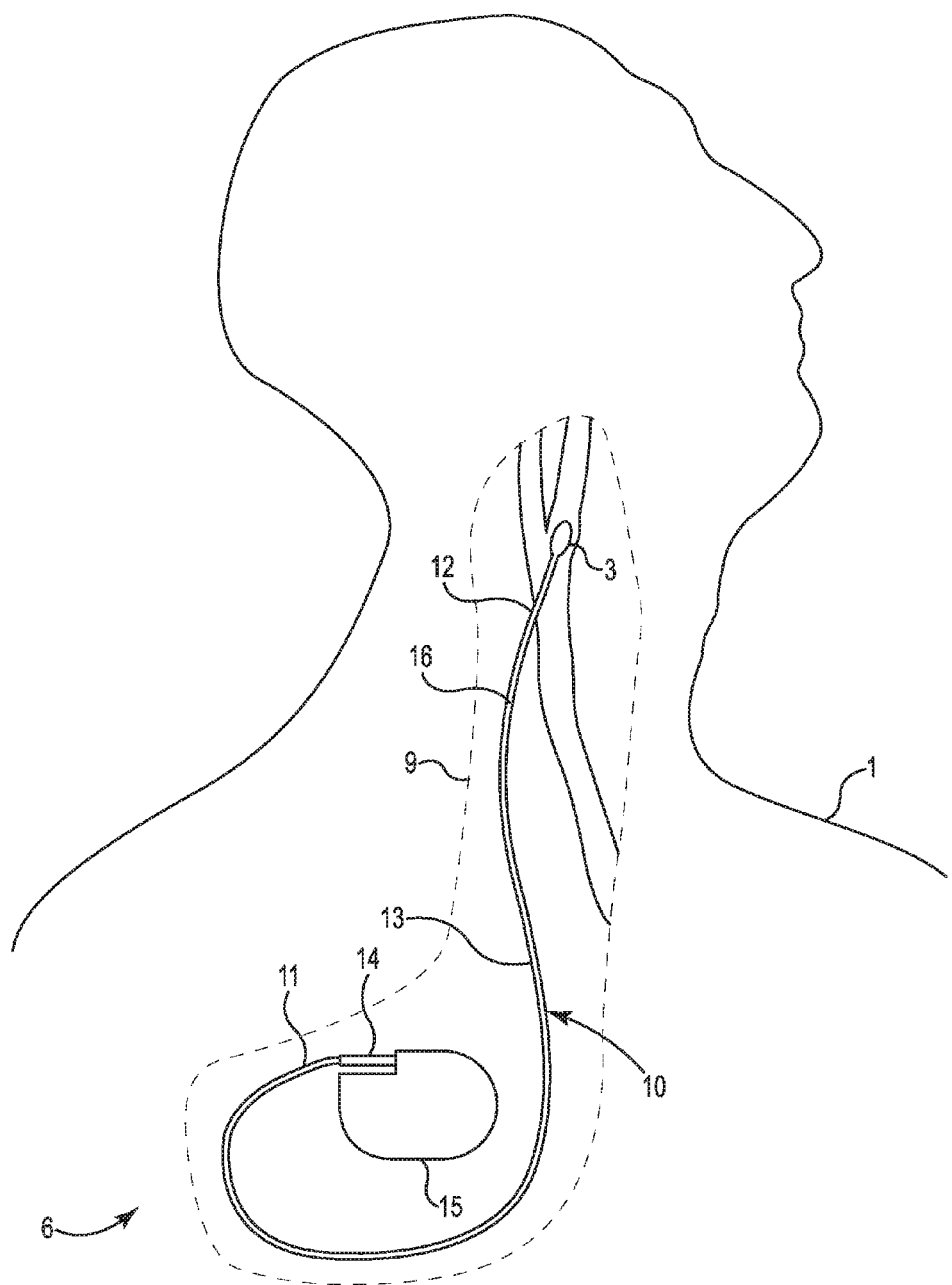
FIG. 1 is a sectional view of a system for stimulating the carotid sinus of a patient.

FIG. 1 is a sectional view of a system 6 for stimulating the carotid sinus of a patient. The system 6 is viewable through the sectional view cutaway 9 over the patient 1. The system 6 can include an implantable pulse generator ("IPG") 15 and a lead 10. The lead 10 can be configured for mounting on the carotid sinus 3 or other anatomical structure within the body. Such mounting can facilitate sensing from and/or stimulating the carotid sinus 3. The IPG 15 can include internal circuitry configured to deliver stimulation energy, such as in the form of electrical pulses. The IPG 15 can additionally or alternatively be configured to sense bioelectrical signals. The IPG 15 can include a receptacle for accepting a connector 14 of the lead 10. The lead 10 can comprise an elongated lead body 16 that includes a proximal portion 11, a distal portion 12, and an intermediate portion 13 between the proximal portion 11 and the distal portion 12. The lead body 16 can be formed from one or more polymeric materials, such as polyurethane and/or silicone, among other materials.

Figure 2:
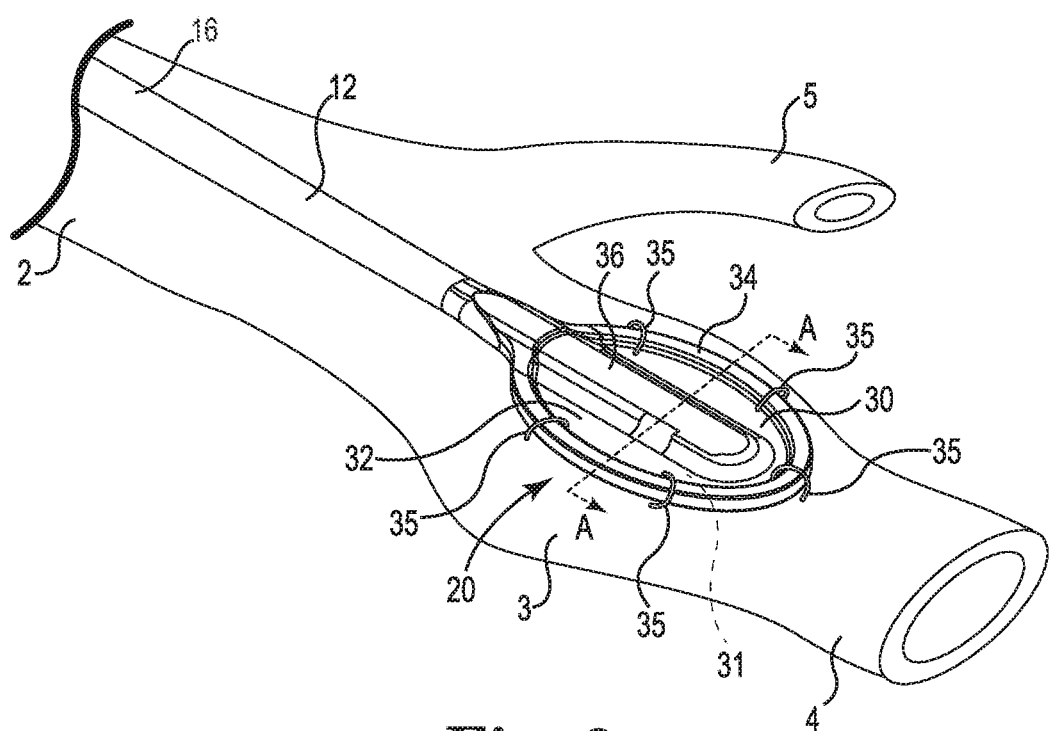
FIG. 2 is isometric view of the distal portion of the lead of FIG. 1 mounted on the carotid sinus.

FIG. 2 is an isometric view of the distal portion 12 of the lead 10 shown in FIG. 1. The distal portion 12 of the lead 10 can include a paddle 20. The paddle 20 can be attached to the lead body 16. The paddle 20 can include a main panel 30. The main panel 30 can include a first face 31 and a second face 32 opposite the first face 31. Either or both of the first face 31 and the second face 32 can be planar or substantially planar. The second face 32 can be coextensive (i.e. overlap) with the first face 31. A ridge 34 can peripherally surround the main panel 30 on at least three sides (e.g., distally, laterally left, and laterally right). As shown in FIG. 2, the ridge 34 can be the radially outermost portion of the paddle 20. The ridge 34 can be raised from the first face 31 of the main panel 30. The ridge 34 can be thicker than the main panel 30 when measured along a common axis, such as an axis orthogonal to the first face 31 and/or the second face 32. The ridge 34 can be raised from the first face 31 of the main panel 30 in the manner of a step. For example, the thickness of the paddle 20 can abruptly transition from the relatively thin main panel 30 to the relatively thick ridge 34. The main panel 30 and the ridge 34 can be formed from one or more polymeric materials, such as polyurethane, silicone, and/or rubber, among other materials.

As shown in FIG. 2, the paddle 20 can include a spine 36. The second face 32 can surround the spine 36 on at least three sides (e.g., distally, laterally left, and laterally right). The spine 36 can house electrical components, as further discussed herein. The spine 36 can be raised from the surface of the first face 31 such that the spine 36 is not flush with the planar or substantially planar profile of the second face 32. The spine 36 can be formed from a polymeric material, such as any polymeric material referenced herein. For example, the spine 36 can be formed from the same material as the main panel 30 and the ridge 34.

The paddle 20 can be sutured in place during a surgical procedure. The paddle 20 can be secured to the carotid sinus 3 by a plurality of sutures 35 that penetrate both the carotid sinus 3 and the paddle 20. As shown in FIG. 2, the sutures 35 can penetrate the main panel 30 radially between the spine 36 and the ridge 34. The relatively thin portion of the main panel 30 between the inner spine 36 and the outer ridge 34 provides a visible target area for a surgeon to thread the sutures 35 through the paddle 20.

The sutures 35 can wrap around the ridge 34 but may not penetrate the ridge 34. The relatively thin main panel 30 may be susceptible to propagation of tears from the sutures 35 having penetrated the main panel 30. However, the ridge 34, being raised from the second face 32 of the main panel 30 and peripherally surrounding the main panel 30, can prevent the sutures 35 from tearing entirely out of the paddle 20. The ridge 34 can form a blunt inward facing surface that opposes the outward propagation of cracks by requiring the cracks to scale the blunt inward facing surface of the ridge 34 before propagating into the ridge 34. While sutures 35 are disclosed as an example herein, other types of surgical fasteners can be used in the same manner to anchor the paddle 20 in place of sutures 35, such as staples.

FIG. 2 shows the distal portion 12 of the lead 10 mounted on the carotid sinus 3. As shown in FIG. 2, the carotid sinus 3 is a bulbous structure of the carotid artery and is located between the internal carotid 4 and the common carotid 2. The external carotid 5 branches from the common carotid 2. The carotid sinus 3 includes nerves which measure the degree of distension of the carotid artery. Normally, these nerves relay bioelectrical information regarding blood pressure in the arterial system as experienced along the carotid sinus 3 to the central nervous system. The central nervous system regulates blood pressure based on this bioelectrical information, such as by changing the heart rate and/or degree of vasoconstriction. The nerves of the carotid sinus 3 can be stimulated by pulses of electrical energy to achieve therapeutic results, such as to lower the blood pressure of the patient 1. Such stimulation can address medical conditions, such as hypertension, by lowering blood pressure.

It may be preferred that the stimulation pulses only affect the nerves of the carotid sinus 3 and do not reach other targets, such as the internal carotid 4, the common carotid 2, or the external carotid 5. The distal portion 12 of the lead 10 includes several features to focus and maintain electrical stimulation on the carotid sinus 3 or other target tissue, as discussed herein.

Figure 3:
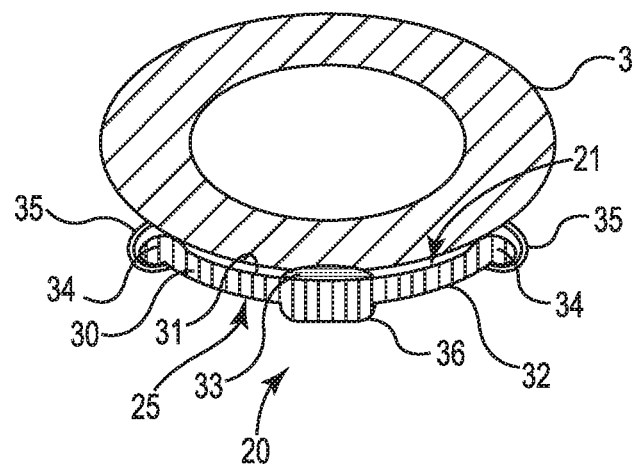
FIG. 3 is a cross-sectional view of the distal portion of the lead of FIG. 2.

FIG. 3 is a cross-sectional view of the distal portion of the lead of FIG. 2 along line AA. The paddle 20 can be orientated such that the first face 31 faces the carotid sinus 3, as shown in FIG. 3. The paddle 20 includes a first broad side 21 and a second broad side 25 opposite the first broad side 21. The paddle 20 includes an electrode 33. The electrode 33 may not be exposed on the second broad side 25. By not exposing the electrode 33 on the second broad side 25, the insulative polymeric material of the paddle 20 can insulate tissue in contact with, or otherwise near, the second broad side 25 from electrical stimulation from the electrode 33 located on the first broad side 21 of the paddle 20. The expanse of the first broad side 21 of the paddle 20 about the electrode 33 (e.g., laterally, proximally, and distally about the electrode 33) can direct electrical stimulation into the carotid sinus 3 or other target tissue by the insulative material of the paddle 20 blocking the electrical stimulation from reaching tissue on the second broad side 25 of the paddle 20 and redirecting the electrical stimulation toward the carotid sinus 3 or other target tissue. The lateral sides of the paddle 20 can curve about the electrode 33 as shown in FIG. 3, to direct electrical stimulation into carotid sinus 3 or other target tissue by the insulative material of the paddle 20 blocking the electrical stimulation from reaching other tissue and redirecting the electrical stimulation toward the carotid sinus 3 or other target tissue. The electrode 33 can be formed from a conductive metal, such as titanium, platinum, palladium, and/or gold, or other conductive material. The electrode 33 may be the only electrode on the distal portion 12 of the lead 10, however other embodiments may include two or more electrodes on the distal portion 12 of the lead 10.

Figure 4:
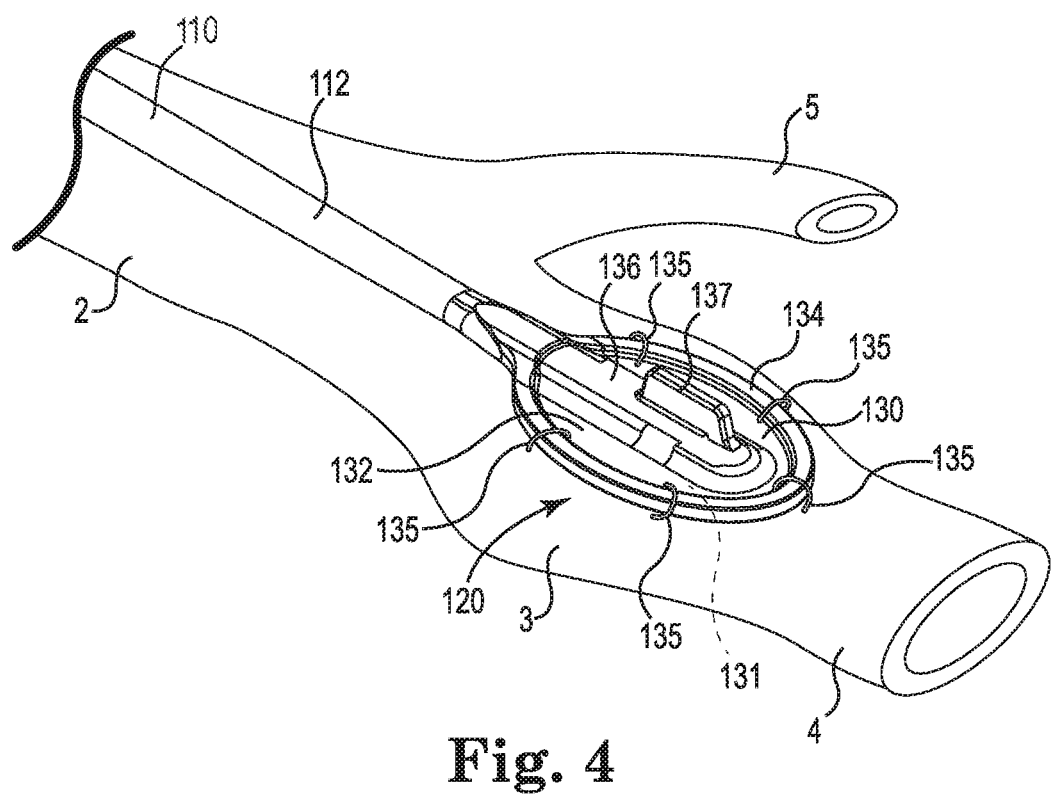
FIG. 4 is isometric view of a distal portion of a lead having a fin.

FIG. 4 is an isometric view of a distal portion 112 of a lead 110. The lead 110 can be configured similarly to any lead disclosed herein, such as lead 10, except where noted. The distal portion 112 includes a paddle 120. The paddle 120 includes a main panel 130. The main panel 130 can include a first face 131 and a second face 132 opposite the first face 131. The paddle 120 further includes a ridge 134 and a spine 136. Sutures 135 can penetrate the main panel 130 and wrap around the ridge 134 to secure the paddle 120 to the carotid sinus 3 or other tissue. The lead 110 can include one or more conductors and one or more electrodes as shown elsewhere herein.

The embodiment of FIG. 4 includes a handle 137. The handle 137 can extend upward from the spine 136. The handle 137 can be formed from the same material as the spine 136. The handle 137 can have the shape of a fin. The handle 137 can be orientated orthogonal with respect to the main panel 130. The handle 137 can be grasped by the surgeon during an implantation procedure, such as with forceps or by hand. The handle 137 can provide a convenient feature for manipulating the distal portion 112 of the lead 110 during suturing while not requiring that the main panel 130 or the ridge 134 of the paddle 120 be directly manipulated.

Figure 5:
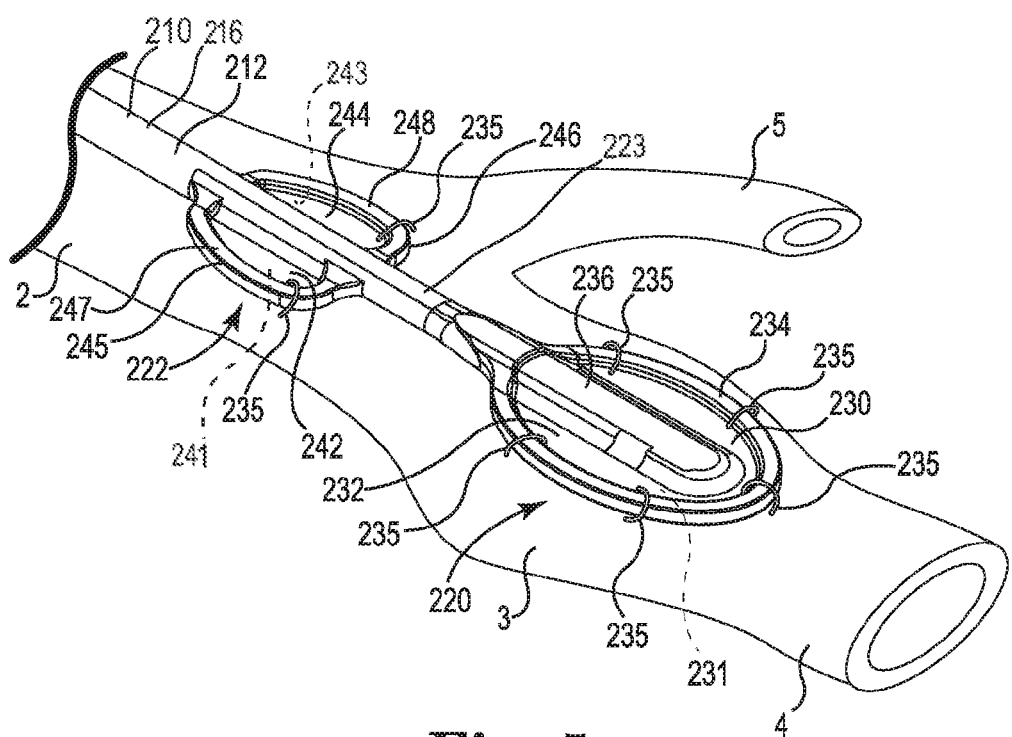
FIG. 5 is isometric view of a distal portion of a lead having a proximal wing.

FIG. 5 is an isometric view of a distal portion 212 of a lead 210. The lead 210 can be configured similarly to any lead disclosed herein, such as lead 10, except where noted. The lead 210 includes a distal portion 212 having a paddle 220. The paddle 220 includes a main panel 230. The main panel 230 can include a first face 231 and a second face 132 opposite the first face 231. The paddle 220 can include a ridge 234. The paddle 220 can include a spine 236. Sutures 235 can penetrate the main panel 230 and wrap around the ridge 234 to secure the paddle 220 to the carotid sinus 3 or other tissue. The lead 210 can include one or more conductors and one or more electrodes as shown elsewhere herein.

The embodiment of FIG. 5 includes a winged portion 222. The winged portion 222 can be positioned on the distal portion 212 of the lead 210. As shown, the winged portion 222 is positioned proximally of the paddle 220. In some embodiments, the winged portion 222 can be separated from the paddle 220 by a neck 223 of the lead body 216. In other embodiments, the winged portion 222 can be directly proximal the paddle 20. The winged portion 222 can include a right wing 245 and a left wing 246. The right wing 245 can be laterally opposite the left wing 246 with respect to the lead body 216. The right wing 245 can include a first face 241 and a second face 242 opposite the first face 241. The left wing 246 can include a first face 243 and a second face 244 opposite the first face 243. When implanted, the distal portion 212 of the lead 210 can be orientated such that the first faces 241, 243 face tissue (e.g., the common carotid 2) to which the winged portion 222 is sutured or otherwise secured. The second faces 242, 244 can face away from the same tissue. The second face 242 of the right wing 245 can be surrounded (e.g., on a distal side, a lateral side, and a proximal side) by a right ridge 247. The right ridge 247 can be raised from the second face 242 in similar manner to the ridge 234 being raised from the second face 232 of the main panel 230. The second face 244 of the left wing 246 can be surrounded (e.g., on a distal side, a lateral side, and a proximal side) by a left ridge 248. The left ridge 248 can be raised from the second face 244 in similar manner to the ridge 234 being raised from the second face 232 of the main panel 230. The right wing 245 can be thinner between the first face 241 and the second face 242 than along the right ridge 247. The left wing 246 can be thinner between the first face 243 and the second face 244 than along the left ridge 248.

The winged portion 222 can be secured to the common carotid 2 by sutures 235. For example, the sutures 235 can penetrate the common carotid 2 and the winged portion 222. As shown in FIG. 5, one or more sutures 235 can penetrate the right wing 245 (e.g., from the first face 241 to the second face 242) inside of the right ridge 247. For example, the right ridge 247 may not be penetrated by any sutures 35 and one or more sutures 235 can wrap around the right ridge 247. One or more sutures 35 can penetrate the left wing 246 (e.g., from the first face 243 to the second face 244) inside of the left ridge 248. For example, the left ridge 248 may not be penetrated by any sutures 235 and one or more sutures 235 can wrap around the left ridge 248. The right ridge 247 and the left ridge 248 can have profiles similar to the ridge 234 of the paddle 220. The right ridge 247 and the left ridge 248 can help prevent suture 235 tear-outs in the same manner as other ridges discussed herein.

Figure 6:
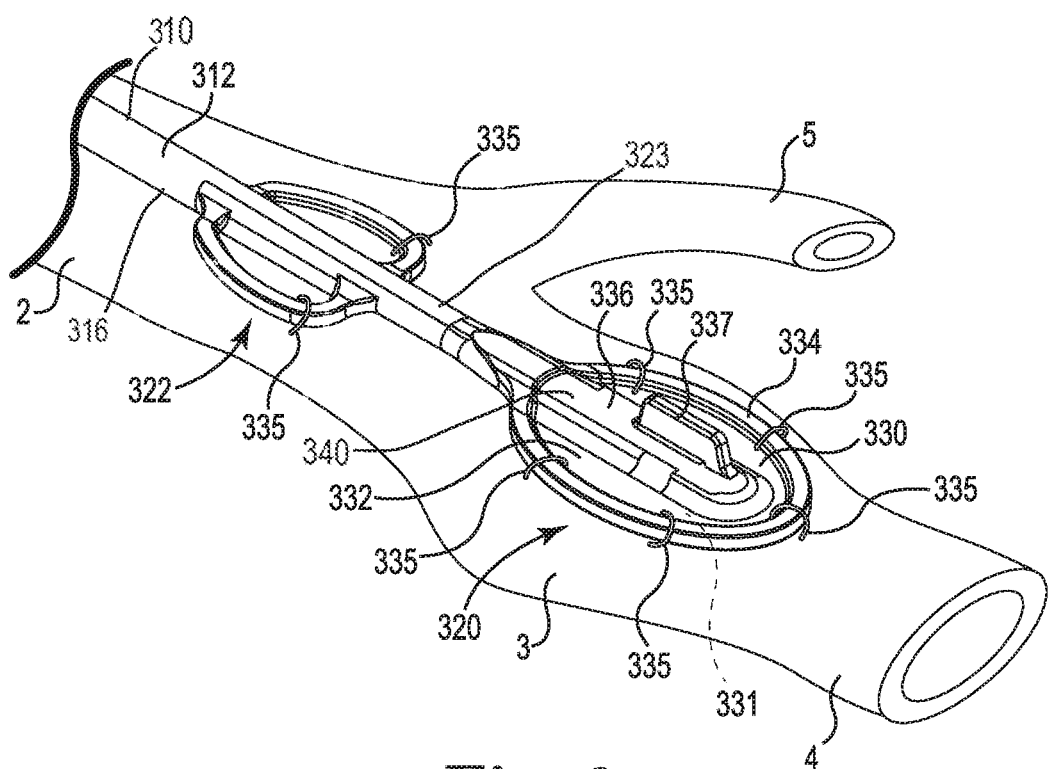
FIG. 6 is isometric view of a distal portion of a lead having a fin and a proximal wing.

FIG. 6 is an isometric view of a distal portion 312 of a lead 310. The lead 310 can be configured similarly to any lead disclosed herein, such as lead 10, except where noted. The lead 310 includes a distal portion 312 having a paddle 320. The paddle 320 includes a main panel 330. The main panel 330 can include a first face 331 and a second face 332 opposite the first face 331. The paddle 320 can include a ridge 334. The paddle 320 can include a spine 336. The spine 336 can include a cover 340. The purpose of the cover 340 is discussed later herein. Sutures 335 can penetrate the main panel 330 to wrap around the ridge 334 to secure the paddle 320 to the carotid sinus 3 or other tissue. A handle 337 can be located on the spine 336 and can project orthogonal to the main panel 330. A winged portion 322 can be located on the lead body 316, proximally of the paddle 320.

Figure 7:
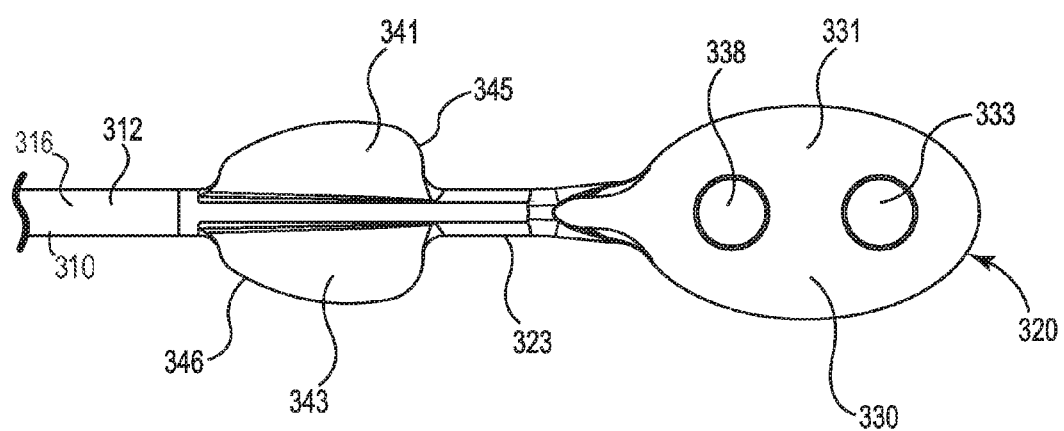
FIG. 7 is an overhead view of the distal portion of the lead of FIG. 6.

FIG. 7 is an overhead view of the distal portion 312 of the lead 310 of FIG. 6. As shown in FIG. 7, the paddle 320 comprises a first electrode 333 and a second electrode 338. Each of the first electrode 333 and a second electrode 338 are located on the first face 331. While the lead 310 of FIGS. 6-7 includes two electrodes on the distal portion 312, a single electrode, or alternatively three or more electrodes, can be provided on the first face 331 of the paddle 320 in other embodiments.

The paddles disclosed herein can be formed in various ways. FIGS. 8-12 demonstrate various manufacturing steps for forming the paddle 320 and other components of the lead 310. While forming the paddle 320 is used as an example, these manufacturing steps can be used to form the other embodiments disclosed herein.

Figure 8:
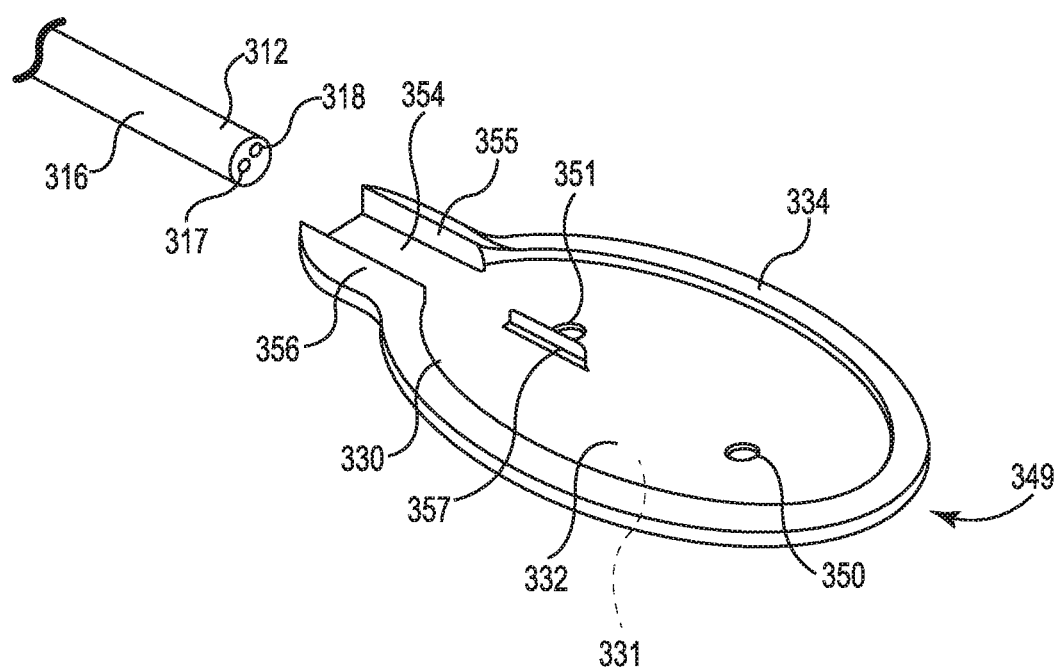
FIG. 8 is isometric view of a molded element.

FIG. 8 shows an isometric view of a planar member 349 and a distal portion of the lead body 316. The lead body 316 can be similar to any lead body disclosed herein. The lead body 316 can include a first lumen 317 and a second lumen 318. The first lumen 317 and the second lumen 318 can extend the full length of the lead body 316.

The planar member 349 can serve as a base component around which the paddle 320 can be formed. In particular, the planar member 349 can comprise the main panel 330 having the first face 331 and the second face 332 opposite the first face 331. The planar member 349 can include the ridge 334. The planar member 349 can have a flat or substantially flat profile. The planar member 349 can be molded from one or more materials, such as one or more types of polymers. The polymers can include one or more of silicone, polyurethane, and rubber, amongst other materials. The planar member 349 can be formed by injection molding. For example, the planar member 349 can be molded with a single shot of polymer material to be a unitary and continuous polymer element. The planar member 349 can include a first through hole 350 and a second through hole 351. The first through hole 350 and the second through hole 351 can extend from the first face 331 to the second face 332. The first through hole 350 and the second through hole 351 can each have the same diameter. Additional embodiments include the planar member 349 including a single through hole, or additional through holes beyond the two illustrated in FIG. 8.

A proximal portion of the planar member 349 can include a first sidewall 355, a second sidewall 356, and a channel 354 defined between the first sidewall 355 and the second sidewall 356. The planar member 349 can include a divider 357. The divider 357 can project upwards from the first face 331. The divider 357 can be in the form of a fin. The divider 357 can separate conductors (discussed further herein) placed along the planar member 349 in a later assembly step.

Figure 9:
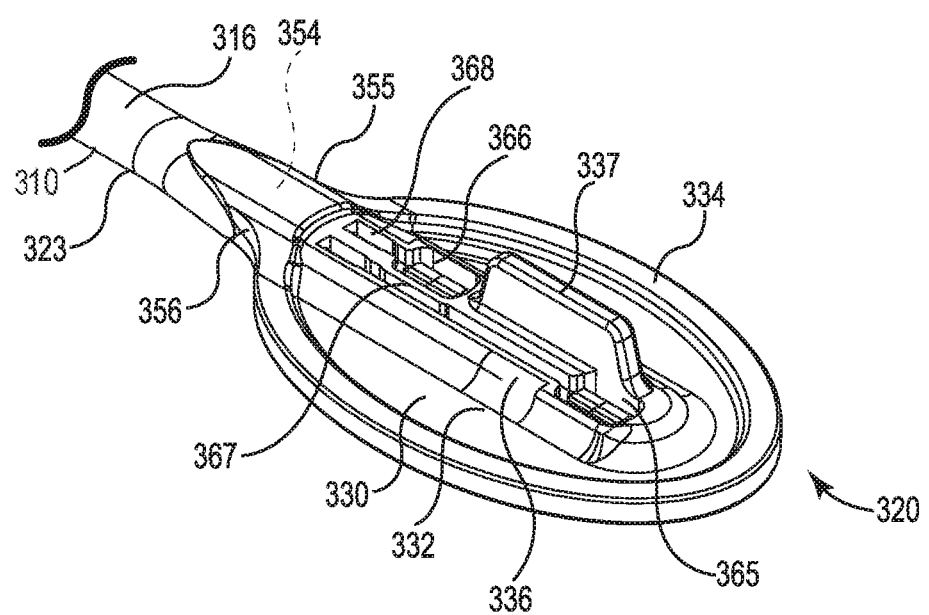
FIG. 9 is an isometric view of the distal portion of a partial assembly of a lead that incorporates the molded element of FIG. 8.

FIG. 9 shows an isometric view of the partially assembled paddle 320. Relative to FIG. 8, the spine 336 has been molded onto the planar member 349 and around the lead body 316. To manufacture the subassembly of FIG. 9, the lead body 316 can be placed in the channel 354 of the planar member 349 between the first sidewall 355 and the second sidewall 356 (shown in FIG. 8). The planar member 349 and part of a lead body 316 can be inserted into a mold and the spine 336 can be molded on the planar member 349. The handle 337, if present on the embodiment, can also be formed in the same molding step from the same material. The molding material can partially form the neck 323 and can bond with the lead body 316 to connect the planar member 349 to the lead body 316. It is noted that, in some embodiments, the spine 336, and further optionally the handle 337, can be molded in the same single shot mold step that forms the planar member 349, such that the spine 336 may not be molded onto the planar member 349.

As shown in FIG. 9, the molding of the spine 336 can include molding the spine 336 to have a first electrode cavity 365, a second electrode cavity 366, a first conductor channel 367, and a second conductor channel 368. The first electrode cavity 365, the second electrode cavity 366, the first conductor channel 367, and/or the second conductor channel 368 can be exposed during assembly, as shown in FIG. 9, to allow manipulation of parts within the spine 336, as further discussed herein.

Figure 10:
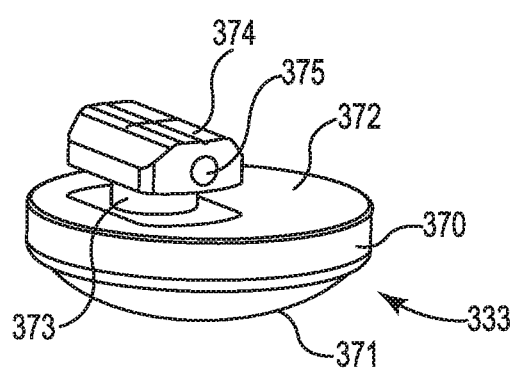
FIG. 10 is isometric view of an electrode.

FIG. 10 is an isometric view of a first electrode 333. The first electrode 333 can be similar to any electrode disclosed herein. The first electrode 333 can include a main body 370. The main body can include a face 371. The face 371 is dome shaped in the embodiment of FIG. 10. It will be understood that the face 371 can alternatively have a different shape, such as a flat shape. The main body 370 includes a back 372 that is opposite the face 371. A post 373 extends from a back 372 of the main body 370. The post 373 is shown to be circular in the embodiment of FIG. 10, however other shapes are possible. The diameter of the post 373 can be the same as, or slightly larger than, the diameter of the first through hole 350 in the planar member 349. A first connector 374 can be connected to the post 373, the first connector 374 on the opposite side of the post 373 with respect to the main body 370.

The first electrode 333 can be mounted on the paddle subassembly of FIG. 9. Specifically, the first connector 374 can be inserted through the first through hole 350 (shown in FIG. 8) of the planar member 349 which forms part of the subassembly of FIG. 9. Each of the first connector 374 and the main body 370 can have a profile larger than the inner diameter of the first through hole 350 such that the first connector 374 snaps through the first through hole 350 and then is held in place on the main panel 330 by the first connector 374 being on the first face 331 of the main panel 330 and being relatively larger than the inner diameter of the first through hole 350, while the main body 370 can be on the second face 332 and also relatively larger than the inner diameter of the first through hole 350. The post 373, being larger in diameter than the first through hole 350, can form a seal between the post 373 and the planar member 349 to prevent intrusion of bodily fluids into the spine 336.

The first connector 374 can be configured to mechanically and electrically connect with a conductor. For example, the first connector 374 includes a lumen 375 which is dimensioned to accommodate a conductor (e.g., the first conductor 381 shown in FIG. 11 and further discussed herein). The first connector 374 can be deformed after the conductor is inserted into the lumen 375. For example, the first connector 374 can be impinged or compressed by a tool (e.g., a pin and/or vise) to crimp the first connector 174 around the conductor within the lumen 375.

Figure 11:
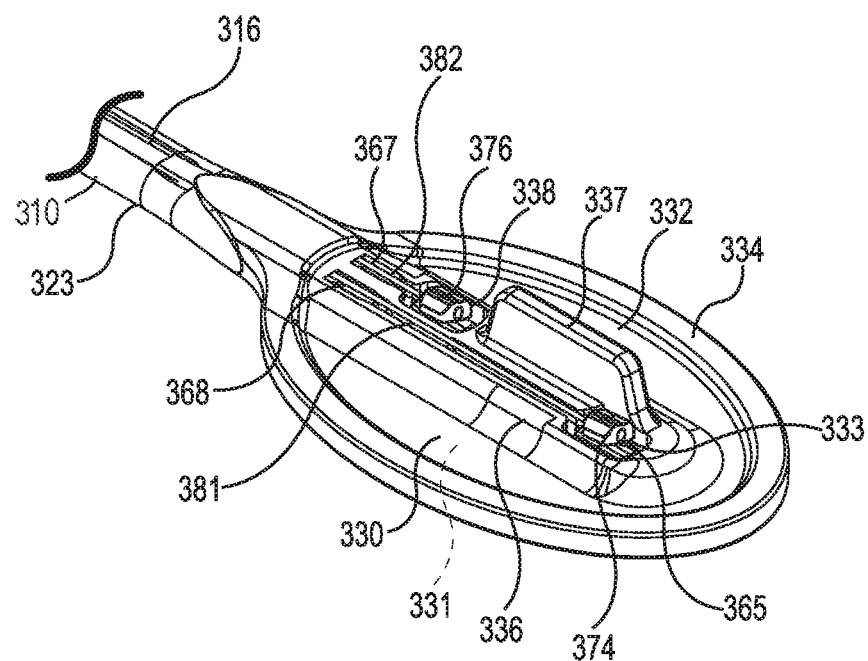
FIG. 11 is an isometric view of the distal portion of the partial assembly of the lead that incorporates the molded element of FIG. 8 and the electrode of FIG. 10.

FIG. 11 shows the first connector 374 of the first electrode 333 having been placed into the first electrode cavity 365. The main body 370 of the first electrode 333 can be along the second face 332 of the main panel 330. A first conductor 381 can be inserted into the first lumen 317 from the proximal portion of the lead body 316 to extend into the first conductor channel 367 and the first electrode cavity 365. The first conductor 381 can also extend into the lumen 375 of the first connector 374 of the first electrode 333 which can also be within the first electrode cavity 365. The first connector 374 can then be crimpled, welded, or by other technique mechanically and electrically connected to the first electrode 333.

The second conductor 382 can be inserted into the second lumen 318 from the proximal portion of the lead body 316 to extend into the second conductor channel 368 and the second electrode cavity 366. A second electrode 338, which can be identical to the first electrode 333, can be mounted on the paddle 320 in the same manner as the first electrode 333, including by being partially placed within the second electrode cavity 366. The second conductor 382 can be placed within the second conductor channel 168 to be inserted into a lumen of the second connector 376 (e.g., similar to lumen 375) of the second electrode 338. The second connector 376 can be deformed as discussed herein to mechanically and electrically connect to the second electrode 338 to the second conductor 382.

Returning to FIG. 6, the cover 340 can be formed within and/or over the first conductor channel 367, the second conductor channel 368, the first electrode cavity 365, and the second electrode cavity 366 to form the paddle 320 shown in FIG. 6. The cover 340 can be a top surface of the spine 336. The cover 340 can be injection molded or applied as an adhesive, among other options. The adhesive can be a medical adhesive, for example. The cover 340 can electrically insulate the first conductor 381, the second conductor 382, the first electrode 333, and the second electrode 338. Such insulation can prevent electrical energy from leaking out of the spine 336 to tissue.

A winged portion, such as the winged portion 322 of FIG. 6, can be injection molded directly onto the lead body 316.

Figure 12:
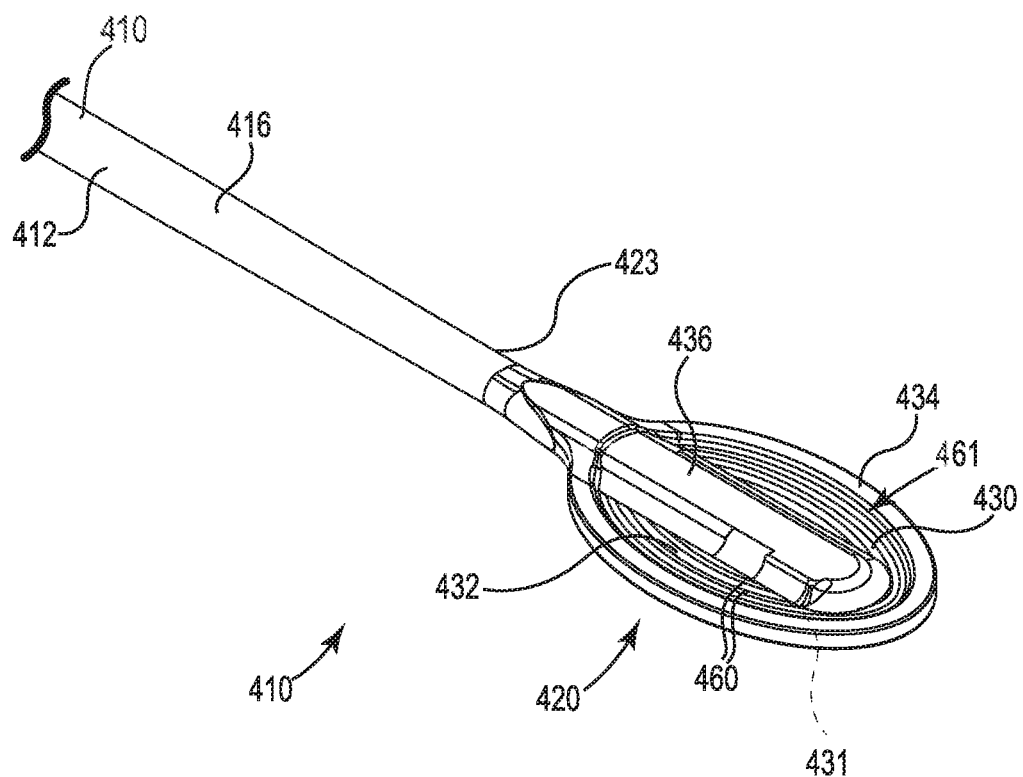
FIG. 12 is an isometric view of a distal portion of a lead having a textured surface.

FIG. 12 is an isometric view of a distal portion 412 of a lead 410. The lead 410 can be configured similarly to any lead disclosed herein, such as leads 10, 210, and 310, except where noted. The distal portion 412 includes a paddle 420 connected to a lead body 416. The paddle 420 includes a main panel 430. The main panel 430 can include a first face 431 and a second face 432 opposite the first face 431. The paddle 420 further includes a ridge 434 and a spine 436. The lead 410 can include one or more conductors and one or more electrodes as demonstrated in connection with other embodiments of this disclosure.

The main panel 430 in the embodiment of FIG. 12 includes a raised pattern 461 on the second face 432. The raised pattern 461 can comprise concentric ovals formed by traces 460. The concentric ovals can be partially complete as shown in FIG. 12. The concentric oval profile of the traces 460 can redirect suture tears from extending laterally (e.g., risking tearing fully out from the paddle 420) to extending concentrically around the spine 436. It can be preferable to redirect the tears in a direction that does not lead to tearing outwardly which may risk a complete tear out of the sutures from the paddle 420. The traces 460 of the raised pattern 461 can be formed into other shapes such as circles, squares, rectangles, grids, and other patterns.

Figure 13:
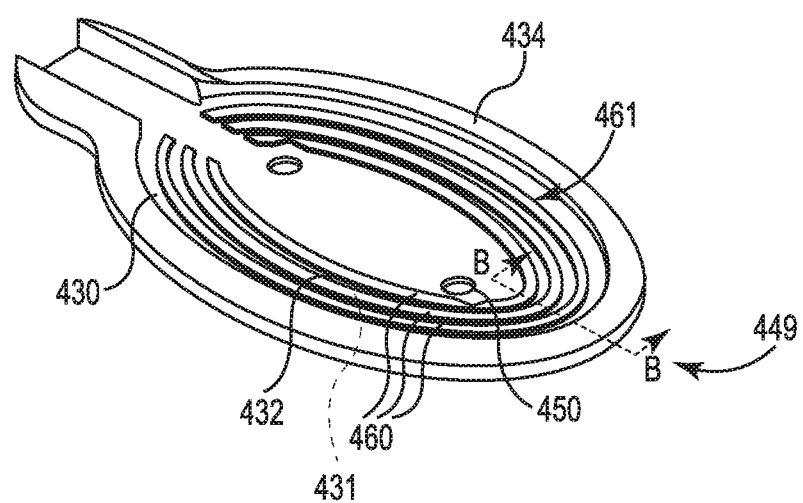
FIG. 13 is isometric view of a molded element of a lead having a textured surface.

FIG. 13 is an isometric view of a planar member 449. The planar member 449 can be configured similarly to any planar member disclosed herein, such as planar member 349, except where noted. The planar member 449 can be used to form the paddle 420 of FIG. 12 in accordance with the manufacturing steps described herein in connection with other embodiments of this disclosure. The planar member 449 includes the raised pattern 461 of traces 460 on the second face 432.

Figure 14:
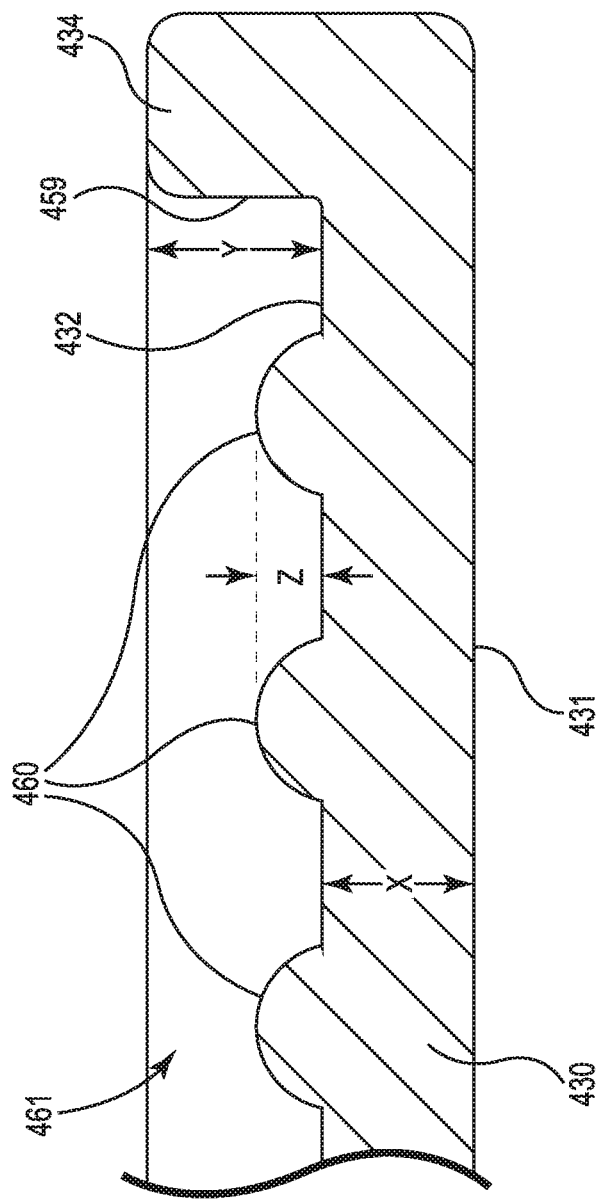
FIG. 14 is a cross sectional view along line BB of FIG. 13.

FIG. 14 shows a cross-sectional view of a portion of the planar member 449 along line BB of FIG. 9. FIG. 14 shows that the first face 431 can be flat. FIG. 14 further shows that the second face 432 can be flat but for the traces 460 (e.g., the second face 432 can be flat in embodiments that do not include the traces 460). FIG. 14 further shows that the thickness of the main panel 430, from the first face 431 to the second face 432, can be equal to a first distance "X". The first distance X can be in the range of, for example, 0.005-0.050 inches (0.127-1.270 millimeters). FIG. 14 further shows that the thickness of the ridge 434, from the second face 432 to the top of the ridge 434, can be equal to a second distance "Y". The second distance Y can be in the range of, for example, 0.001-0.050 inches (0.0254-1.270 millimeters). FIG. 14 further shows that the thickness of the traces 460, from the second face 432 to the top of each trace 460, can be equal to a third distance "Z". The third distance Z can be in the range of, for example, 0.001-0.050 inches (0.0254-1.270 millimeters). It is noted that the first distance X can be less than the second distance Y. In some embodiments, however, the first distance X and the second distance Y may be equal. In some other embodiments, the first distance X is greater than the second distance Y. It is noted that the above dimensions can be applied to similar portions of any embodiment of the present disclosure. In some embodiments, the traces 460 can be raised to the same height as the ridge 434 or can be raised higher than the ridge 434. It is noted that each of the distances X, Y, and Z can be measured orthogonal to the planar orientation of the planar member 449. The distances X, Y, and Z can be measured orthogonal to the planar orientation of the first face 431 and/or the second face 432.

The difference between the first distance X and the second distance Y can balance the flexibility of the main panel 430 with prevention of suture tear propagation. The traces 460 can prevent propagation of some tears but, to the extent that they are less thick than the ridge 434, provide less protection from tear propagation than the ridge 434. The ridge 434 can also block tears by having a step 459 from the second face 432 to the ridge 434. The sheer face of the step 459 can blunt tears propagating along the second face 432 when the tears reach the step 459. The inward facing surface of the step 459 can be orientated orthogonal to the main panel 430. More specifically, the inward facing surface of the step 459 can be orientated orthogonal to the flat surface of the second face 432.

Figure 15:
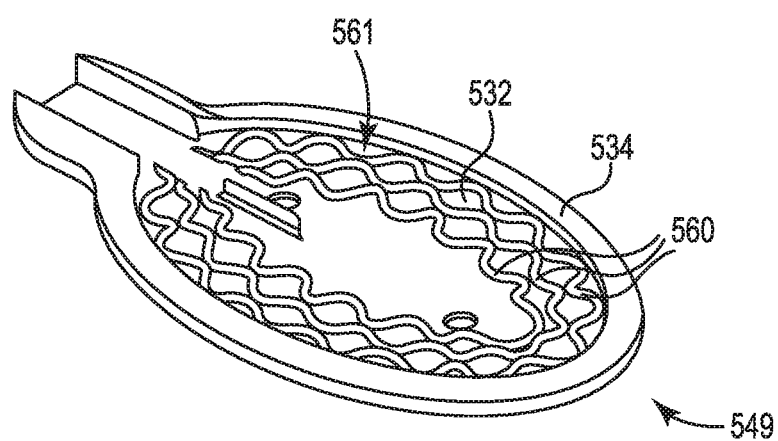
FIG. 15 is an isometric view of a molded element of a lead.

FIG. 15 is an isometric view of a planar member 549. The planar member 549 can be configured similarly to any planar member disclosed herein, such as planar member 349 and/or 449, except where noted. The planar member 549 can be used to form a paddle in any manner described herein in connection with other embodiments of this disclosure. The planar member 549 includes a raised pattern 561 of traces 560 on the second face 532. The traces 560 have a waved shape as compared to the non-waving concentric ovals of the raised pattern 461 of the embodiment of FIGS. 12-13. The planar member 549 includes a ridge 534 which can be similar in form and function to any ridge disclosed herein.

Figure 16:
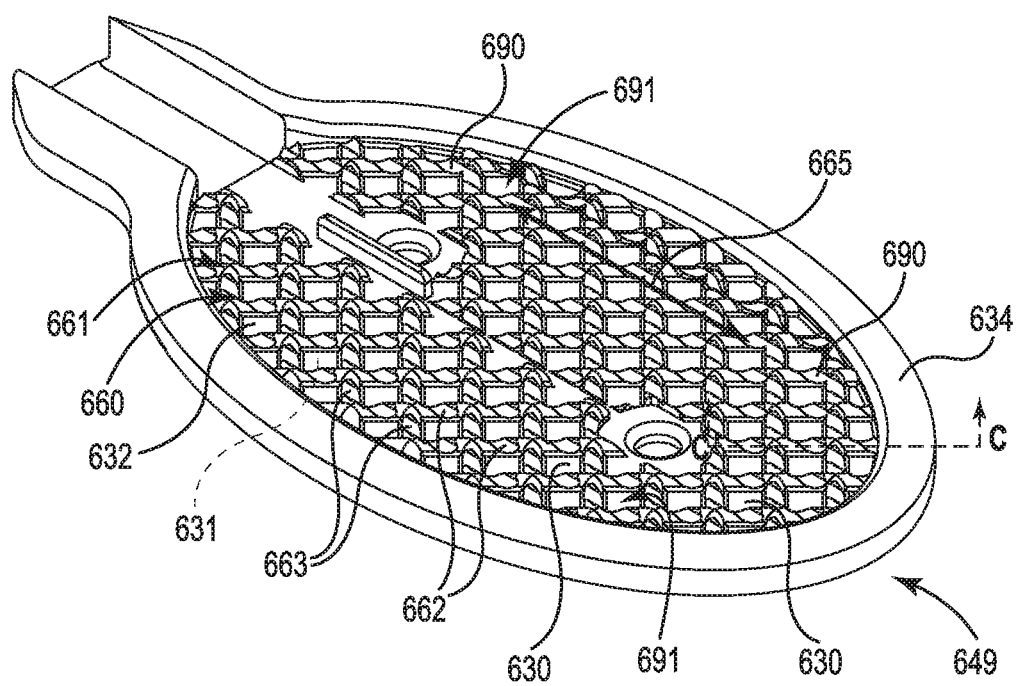
FIG. 16 is an isometric view of a molded element of a lead.

FIG. 16 shows an isometric view of a planar member 649. The planar member 649 can be incorporated into any lead shown herein. The planar member 649 can comprise a main panel 630 having a first face 631 and a second face 632 opposite the first face 631. The main panel 630 can be peripherally surrounded by a ridge 634. The raised pattern 661 of the embodiment of FIG. 16 can include a plurality of traces 660. The plurality of traces 660 can include first set of traces 662 and a second set of traces 663. The first set of traces 662 can comprise a plurality of parallel traces of material of the planar member 649 raised above the second face 632. The second set of traces 663 comprises a plurality of parallel traces 660 of material of the planar member 649 raised above the second face 632. The first set of traces 662 and the second set of traces 663 can form a crossing pattern. The first set of traces 662 can be orientated orthogonal to the second set of traces 663. The crossing pattern creates a plurality of cells 691, each cell 691 defined by the first and second sets of traces 662, 663. A suture or other fastening element can penetrate the main panel 630 through a cell 691, between the traces 660 that define the cell 691, such that the traces 660 themselves are not penetrated by the suture or other fastening element. The traces 660 surrounding each cell 691 provide protection from tear propagation from the suture or other fastening element.

The raised pattern 661 can include a secondary pattern. The secondary pattern can comprise a plurality of grooves 690 that are sunken into the traces 660 of the raised pattern 661. As shown, the plurality of grooves 690 are arranged into a plurality of axially aligned sets, the sets extending parallel with one another. One such set, for example, is arrayed along longitudinal axis 665. Each set of axially aligned grooves forms a seam to increase the flexibility of the main panel 630 in a direction orthogonal to the axial orientation of the axially aligned grooves. The grooves 690 can be aligned along the longitudinal axis of the main panel 630 but may not be aligned along an axis transverse to the main panel 630 (i.e. the grooves 690 are not aligned along a width dimension of the planar member 649). Such a pattern of grooves 690 promotes bending of the main panel 630 around a longitudinal axis of a paddle (e.g., such as in the manner shown in FIG. 3) while the main panel 630 resists bending about other axes, such as resisting bending about a width axis.

Figure 17:
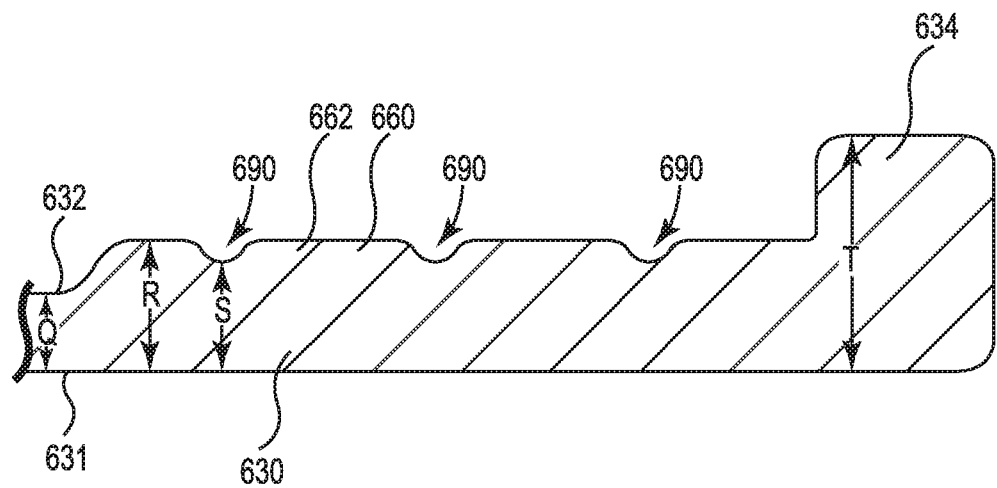
FIG. 17 is a cross-sectional view of a portion of the molded element of FIG. 16.

FIG. 17 shows a cross-sectional view of the planar member 649 along line CC of FIG. 16. The cross section of FIG. 17 shows that a trace 660 from the first set of traces 662 is raised from the second face 632 of the main panel 630. The cross section of FIG. 17 further shows that the grooves 690 in the trace 662 reduce the height of the trace 662 but the grooves 690 in the trace 662 do not extend all the way back down to the first face 631 of the main panel 630. In this way, the main panel 630 can have a thickness "Q" between the first face 631 and the second face 632, a thickness "R" between the top of each trace 662 and the first face 631, a thickness "S" between the bottom of one or more of the grooves 690 and the first face 631, a thickness "T" between the top of the ridge 634 and the first face 631. The thickness "T" can be larger than any of the thickness Q, the thickness R, or the thickness S. The thickness R can be greater than any of the thickness Q or the thickness S. The thickness S can be greater than the thickness Q. In some embodiments, the thickness S is equal to, or less than, the thickness Q. For example, the grooves 690 may extend down to the second face 632 or even lower than the second face 632. In some other embodiments, the grooves 690 are formed directly on the second face 632 (e.g., with or without the traces 660) such that the grooves are sunken below the second face 632. In some embodiments, the grooves 690 are formed in both the second face 632 and the raised pattern 661. It is noted that each of the distances Q, R, S, and T can be measured orthogonal to the planar orientation of the planar member 649. Being that the planar member 649 is used to form a paddle, any of the distances Q, R, S, and T can be measured orthogonal to the planar orientation of the paddle. The distances Q, R, S, and T can be measured orthogonal to the planar orientation of the first face 631 and/or the second face 632.

While various embodiment concern lead embodiments that connect with a conventional IPG, various other embodiments can concern leadless paddle designs. For example, the paddle 20 of FIGS. 1-3 (or any paddle presented herein) can be modified to not include the lead body 16. The circuitry for sensing signals and/or delivering stimulation, normally located within the IPG 15, can be relocated to be contained within the spine 36. The circuitry can electrically connect with the electrode 33, or more electrodes if more electrodes are provided in the embodiment. The leadless paddle can be attached to tissue, such as along the epicardium, by wrapping one or more sutures around the ridge 34 of the leadless paddle.

The manner of presenting illustration and descriptions of embodiments herein is done in an exemplary format that concisely demonstrates different combinations of features. These embodiments are not to be understood as mutually exclusive, nor should the features of different embodiments be understood to be mutually exclusive. It is noted that any of the elements having similar names and base reference numbers (e.g., paddle 20 and paddle 120) can have similar characteristics even if not expressly stated. Therefore, a characteristic presented in connection with one embodiment can be applied to other embodiment having a similar name and reference number, although it is noted that not all possible shared characteristics are identified in this manner. Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as falling within the scope of the claims, together with all equivalents thereof.

The following is claimed:

1. An implantable lead comprising:
   an elongated lead body having a proximal portion and a distal portion;
   at least one conductor extending within the elongated lead body;
   at least one electrode electrically connected to the at least one conductor; and
   a paddle attached to the distal portion of the lead body, the paddle comprising:
      a main panel;
      a ridge on a periphery of the main panel; and
      a raised pattern of traces, the main panel comprising a first face and a second face opposite the first face, each of the at least one electrode exposed on the first face but not exposed on the second face, wherein the paddle is thicker along the ridge than along the main panel; and the raised pattern of traces is formed on the second face.

2. The lead of claim 1, wherein the ridge is raised from the first face of the main panel.

3. The lead of claim 1, wherein the paddle comprises a distal side, a first lateral side, and a second lateral side opposite the first lateral side, and wherein the ridge peripherally surrounds the main panel on the distal side, the first lateral side, and the second lateral side of the paddle.

4. The lead of claim 3, wherein the first and the second lateral sides are configured to wrap partially around an anatomical structure.

5. The lead of claim 4, wherein the anatomical structure is a blood vessel.

6. The lead of claim 1, wherein the main panel, the traces, and the ridge are formed from a first polymeric material.

7. The lead of claim 1, wherein the ridge has greater tear resistance than the main panel.

8. The lead of claim 1, wherein the main panel, the ridge, and the raised pattern of traces form a unitary member that is molded from a first polymeric material.

9. The lead of claim 1, wherein the ridge is raised higher above the second face than the raised pattern of traces.

10. The lead of claim 1, wherein the raised pattern of traces comprises a plurality of concentric ovals.

11. The lead of claim 1, wherein the raised pattern of traces comprises a grid pattern of a first set of parallel traces that intersect a second set of parallel traces.

12. The lead of claim 1, wherein a plurality of grooves are formed through the raised pattern of traces, the plurality of grooves extending parallel with a longitudinal axis of the paddle.

13. The lead of claim 1, wherein:
   the paddle is configured to be secured to tissue by at least one suture that extends through the main panel from the first face to the second face, and
   the ridge is configured to block propagation of tears in the main panel due to the at least one suture from propagating through the ridge.

14. The lead of claim 1, further comprising a winged portion attached to the lead body, the winged portion located proximally of the paddle, the winged portion comprising a first wing and a second wing laterally opposite the first wing, wherein each of the first wing and the second wing comprise an inner portion and an outer portion that surrounds the inner portion, the inner portion thinner than the outer portion.

15. An implantable device comprising:
   at least one electrode; and
   a paddle including the at least one electrode and a planar member attached to the at least one electrode, the planar member comprising:
      a main panel;
      a raised pattern of traces formed on the main panel; and
      a ridge on a periphery of the main panel, each of the at least one electrode exposed on a face of the main panel, the ridge thicker than the main panel.

16. The device of claim 15, wherein the planar member comprises a step that transitions the relatively thinner main panel to the relatively thicker ridge.

17. The device of claim 15, wherein:
   the paddle is configured to be secured to tissue by at least one suture that extends through the main panel, and
   the ridge is configured to block propagation of tears in the main panel from propagating through the ridge.

18. The device of claim 15, wherein the traces comprises a plurality of concentric ovals.

19. The device of claim 15, wherein the traces comprises a grid pattern of a first set of parallel traces that intersect a second set of parallel traces.

20. The device of claim 15, wherein a plurality of grooves are formed through the traces, the plurality of grooves extending parallel with a longitudinal axis of the paddle.

21. The device of claim 15, wherein the main panel, the traces, and the ridge are formed from a single polymeric material.

22. The device of claim 21, wherein the main panel, the traces, and the ridge form a unitary member that is molded from the single polymeric material.

23. A method of implanting a lead, the method comprising:
introducing an elongated lead into a patient, the lead comprising a paddle that comprises a main panel, a ridge that peripherally surrounds the main panel, and a raised pattern of traces formed on the main panel, wherein the paddle is thicker along the ridge and the traces than along the main panel;
wrapping opposing lateral sides of the paddle partially around an anatomical structure; and
suturing the paddle to the anatomical structure with a plurality of sutures, each of the sutures threaded through the main panel but not through the ridge or the traces, wherein the ridge and the traces are configured to block propagation of tears in the main panel from propagating through the ridge and the traces.

24. The method of claim 23, wherein the lead further includes a winged portion located proximally of the paddle, the winged portion including a first wing and a second wing, the second wing laterally opposite the first wing, each of the first wing and the second wing include an inner portion and an outer portion that surrounds the inner portion, the inner portion thinner than the outer portion, the method further comprising:
wrapping the first wing and the second wing partially around the anatomical structure; and
suturing the winged portion to the anatomical structure with a plurality of sutures, each of the sutures threaded through the first wing or the second wing, but not through the outer portion of either of the first wing or the second wing, wherein the outer portion of the first wing or the second wing is configured to block propagation of tears in the winged portion from propagating through the outer portion of the first wing or the second wing.

25. An implantable lead comprising:
an elongated lead body having a proximal portion and a distal portion;
at least one conductor extending within the elongated lead body;
at least one electrode electrically connected to the at least one conductor;
a paddle attached to the distal portion of the lead body, the paddle comprising:
a main panel comprising a first face and a second face opposite the first face, each of the at least one electrode exposed on the first face but not exposed on the second face; and
a ridge on a periphery of the main panel, wherein the paddle is thicker along the ridge than along the main panel; and
a winged portion attached to the lead body, the winged portion located proximally of the paddle and including:
a first wing; and
a second wing, the second wing laterally opposite the first wing.

26. The lead of claim 25, wherein the paddle comprises a distal side, a first lateral side, and a second lateral side opposite the first lateral side, and wherein the ridge peripherally surrounds the main panel on the distal side, the first lateral side, and the second lateral side of the paddle.

27. The lead of claim 25, wherein the main panel and the ridge are formed by a unitary member that is molded from a polymeric material.

28. The lead of claim 25, wherein each of the first wing and the second wing include an inner portion and an outer portion that surrounds the inner portion, the inner portion thinner than the outer portion.

29. The lead of claim 28, wherein the paddle is configured to be secured to tissue by at least one suture that extends through the main panel and at least one suture that extends through the winged portion, the ridge configured to block propagation of tears through the main panel, and the outer portion of each of the first wing and the second wing configured to block propagation of tears through the winged portion.

30. The lead of claim 25, wherein the paddle further includes a raised pattern of traces formed on the second face.

31. The lead of claim 30, wherein the main panel, the ridge, and the raised pattern of traces form a unitary member that is molded from a single polymeric material.

32. The lead of claim 30, wherein the raised pattern of traces comprises a plurality of concentric ovals.

33. The lead of claim 30, wherein the raised pattern of traces comprises a plurality of waved shapes.

34. The lead of claim 30, wherein the raised pattern of traces comprises a grid pattern of a first set of parallel traces that intersect a second set of parallel traces.

35. The lead of claim 30, wherein a plurality of grooves are formed through the raised pattern of traces, the plurality of grooves extending parallel with a longitudinal axis of the paddle.

* * * * *